United States Patent
Li et al.

(10) Patent No.: US 11,033,183 B2
(45) Date of Patent: Jun. 15, 2021

(54) WIRELESS MAGNETICALLY STEERABLE ENDOSCOPE

(71) Applicant: The Chinese University of Hong Kong, Shatin (CN)

(72) Inventors: Zheng Li, Shatin (CN); Calvin Sze Hang Ng, Shatin (CN); Philip Wai Yan Chiu, Shatin (CN); Joseph Jao Yiu Sung, Shatin (CN)

(73) Assignee: The Chinese University of Hong Kong, Hong Kong (CN)

( * ) Notice: Subject to any disclaimer, the term of this patent is extended or adjusted under 35 U.S.C. 154(b) by 309 days.

(21) Appl. No.: 16/071,443

(22) PCT Filed: Jan. 19, 2017

(86) PCT No.: PCT/CN2017/071650
§ 371 (c)(1),
(2) Date: Jul. 19, 2018

(87) PCT Pub. No.: WO2017/125036
PCT Pub. Date: Jul. 27, 2017

(65) Prior Publication Data
US 2019/0159668 A1    May 30, 2019

Related U.S. Application Data

(60) Provisional application No. 62/280,487, filed on Jan. 19, 2016.

(51) Int. Cl.
*A61B 1/313* (2006.01)
*A61B 1/00* (2006.01)
(Continued)

(52) U.S. Cl.
CPC ........ *A61B 1/3132* (2013.01); *A61B 1/00016* (2013.01); *A61B 1/0051* (2013.01);
(Continued)

(58) Field of Classification Search
CPC ... A61B 1/3132; A61B 34/73; A61B 1/00016; A61B 1/00066; A61B 1/00071; A61B 1/00158; A61B 1/0051
See application file for complete search history.

(56) References Cited

U.S. PATENT DOCUMENTS 6,902,528 B1   6/2005  Garibaldi et al.
7,097,615 B2   8/2006  Banik et al.
(Continued)

FOREIGN PATENT DOCUMENTS

CN    101322639 A    12/2008
CN    101322640 A    12/2008

OTHER PUBLICATIONS

Chiu, et al. "Transgastric endoluminal gastrojejunostomy: technical development from bench to animal study (with video)." Gastrointestinal endoscopy 71, No. 2 (2010): 390-393.
(Continued)

*Primary Examiner* — Timothy J Neal
*Assistant Examiner* — Jae Woo
(74) *Attorney, Agent, or Firm* — Kilpatrick Townsend & Stockton LLP (57) ABSTRACT

A new steerable endoscope for minimally invasive surgery is provided. The endoscope system includes: a wireless steerable endoscope (1), an external magnetic controller (2) and an image/video display (3). The wireless steerable endoscope (1) could be inserted through an incision (4-1) on the body skin (4) and be anchored/steered inside the body cavity by the external magnetic controller (2). It is shaftless, wireless, and can be steered inside the body, operating in a remote manner. Compared with existing endoscopes, it neither requires additional incision nor does it occupy trocar or port space. Without the endoscope shaft, the surgical access trauma and incision size can potentially be reduced, avoiding endoscope-instrument fencing. It can be placed
(Continued)

remotely from the access incision, providing an improved and wider field of view. It is soft-bodied and compact in structure, therefore safety is high. More than one wireless endoscope can be placed into the operating cavity, providing simultaneous multiple video images of different viewing angles. These features allow safer, more efficient and less traumatic surgery by reducing trocar size or number.

24 Claims, 10 Drawing Sheets

(51) Int. Cl.
*A61B 1/005* (2006.01)
*A61B 34/00* (2016.01)
*A61B 1/05* (2006.01)
*A61B 34/30* (2016.01)

(52) U.S. Cl.
CPC ........ *A61B 1/0052* (2013.01); *A61B 1/00066* (2013.01); *A61B 1/00071* (2013.01); *A61B 1/00096* (2013.01); *A61B 1/00158* (2013.01); *A61B 1/05* (2013.01); *A61B 34/73* (2016.02); *A61B 2034/302* (2016.02)

(56) References Cited

U.S. PATENT DOCUMENTS

| | | | |
|---|---|---|---|
| 8,084,898 B2 | 12/2011 | Kawano et al. | |
| 8,475,359 B2* | 7/2013 | Asada | A61B 1/3132 600/102 |
| 2007/0161855 A1 | 7/2007 | Mikkaichi et al. | |
| 2008/0058989 A1 | 3/2008 | Oleynikov et al. | |
| 2008/0312500 A1* | 12/2008 | Asada | A61B 1/051 600/109 |
| 2009/0082627 A1* | 3/2009 | Karasawa | A61B 1/00158 600/118 |
| 2009/0198099 A1 | 8/2009 | Myers | |
| 2010/0076259 A1* | 3/2010 | Asada | A61B 1/3132 600/102 |
| 2010/0113872 A1 | 5/2010 | Asada et al. | |
| 2011/0071473 A1* | 3/2011 | Rogers | A61B 17/3423 604/167.01 |
| 2011/0082365 A1* | 4/2011 | McGrogan | A61B 1/00154 600/424 |
| 2011/0261183 A1 | 10/2011 | Ma et al. | |
| 2011/0285488 A1 | 11/2011 | Scott et al. | |

OTHER PUBLICATIONS

Chiu, et al. "Feasibility of full-thickness gastric resection using master and slave transluminal endoscopic robot and closure by Overstitch: a preclinical study." Surgical endoscopy 28, No. 1 (2014): 319-324.

Keller, et al., "Method for navigation and control of a magnetically guided capsule endoscope in the human stomach." In Biomedical Robotics and Biomechatronics (BioRob), 2012 4th IEEE RAS & EMBS International Conference on, pp. 859-865. IEEE, 2012.

Li, et al., "Will the robot take over endoscopy?." Endoscopy 47, No. 09 (2015): 773-774.

Liu, et al., "Design of a unified active locomotion mechanism for a capsule-shaped laparoscopic camera system." In Robotics and Automation (ICRA), 2014 IEEE International Conference on, pp. 2449-2456. IEEE, 2014.

Luo, et al., "Simulation, design, and analysis for magnetic anchoring and guidance of instruments for minimally invasive surgery." In Medical Imaging 2012: Image-Guided Procedures, Robotic Interventions, and Modeling, vol. 8316, p. 83162K. International Society for Optics and Photonics, 2012.

Ng, et al. "Evolution in surgical approach and techniques for lung cancer." Thorax (2013): thoraxjnl—2012.

Ng, et al. "Single port video-assisted thoracic surgery: advancing scope technology." European Journal of Cardio-Thoracic Surgery 47, No. 4 (2014): 751-751.

Ng, et al. "Uniportal and single-incision video-assisted thoracic surgery: the state of the art." Interactive cardiovascular and thoracic surgery 19, No. 4 (2014): 661-666.

Ren, et al., "Computer-assisted transoral surgery with flexible robotics and navigation technologies: A review of recent progress and research challenges." Critical Reviews™ in Biomedical Engineering 41, No. 4-5 (2013).

Vitiello, et al., "Emerging robotic platforms for minimally invasive surgery." IEEE reviews in biomedical engineering 6 (2013): 111-126.

International Search Report in PCt/CN2017/071650, dated Apr. 24, 2017.

* cited by examiner

WIRELESS MAGNETICALLY STEERABLE ENDOSCOPE

REFERENCES TO RELATED APPLICATIONS

This application is a U.S. National Stage Application based on PCT/CN2017/071650, international filing date Jan. 19, 2017, which claims the benefit of priority of U.S. Provisional Application 62/280,487 filed Jan. 19, 2016, the entire contents of which are incorporated by reference herein for all purposes.

FIELD OF THE INVENTION

The invention relates generally to the field of medical devices and their use. More specifically, it provides a system that comprises a wireless endoscope, a magnetic controller, and a monitoring subsystem.

BACKGROUND

Minimally invasive surgery (MIS) is becoming the standard of care in a wide range of surgical operations. Endoscopes provide real-time image/video of the surgical site, which cannot be seen directly by the surgeons. The demand for suitable endoscopes has increased significantly due to the prevalence of MIS. The global market for endoscopy equipment is estimated $28.2 billion in 2013 and is expected to reach $37.9 billion in 2018.

Existing endoscopes include the rigid/semi-rigid endoscope, flexible endoscope and capsule endoscope. Rigid endoscope have a straight shaft with the imaging module in the front. Semi-rigid endoscope, like the EndoEye Flex™ of Olympus, contains a rigid shaft and a bending section. The camera is installed in the distal end of the bending section. These two types of endoscopes are most frequently used in conventional MIS. In the procedure, the endoscope requires an additional incision port to insert into the surgical site and the endoscope shaft cannot be removed during the operation while image/video from the endoscope is required. This incision brings additional surgical access trauma to the patient, impairs the postoperative cosmesis and can be an additional source of chronic pain after the surgery.

Laparo-Endoscopic Single-Site (LESS) or Single Port Access (SPA) surgery allows the endoscope to be inserted via the same incision as the other operating instruments. However, the shaft of the endoscope makes the crowded surgical site even worse, and causes endoscope-instrument fencing and interference. The endoscope obstructs the surgeon's operation and may collide with the other instruments sharing the same incision.

Flexible endoscopes are mostly used in natural orifice inspection and operation. For example, the gastroscope and colonoscope are used in the gastrointestinal (GI) tract inspection, while the bronchoscope is used to view the bronchi. These endoscopes are rarely used in MIS, LESS or SPA surgery as the shaft is difficult to be steered without the lumen. Their revisions could possibly be used in natural orifice transluminal surgery (NOTES), such as the R-scope™ made by Olympus. Another type of endoscopic device, the capsule endoscope is pill-like. It is dedicatedly used in GI tract inspection. Conventionally, they could only move passively with the GI peristalsis. Efforts have been made to develop active capsule endoscopes, such as by mimicking swimming, crawling, padding, or magnetic dragging.

Information that was published before the filing of this disclosure includes the following:

U.S. Pat. No. 7,097,615 B2: Robotic Endoscope with Wireless Interface, Aug. 29, 2006

U.S. pre-grant publication 2008/0058989 A1: Surgical Camera Robot, Mar. 6, 2008

U.S. pre-grant publication 2008/0058989 A1: Wireless Laparoscopic Camera', Oct. 27, 2011

Haifeng Luo, Emmanuel Wilson and Kevin Cleary, "Simulation, design and analysis for magnetic anchoring and guidance of instruments for minimally invasive surgery", SPIE Medical Imaging, International Society for Optics and Photonics, pp. 8316K-8316K-6, 2012

Xiaolong Liu, Gregory J. Mancini and Jindong Tan, "Design of a Unified Active Locomotion Mechanism for A Wireless Laparoscopic Camera System", IEEE/RSJ International Conference on Intelligent Robots and Systems (IROS), pp. 1294-1301, Sep. 14-18, 2014, Chicago, Ill., USA Li Zheng, Chiu Philip W. Y., "Will the robot take over endoscopy?", Endoscopy, pp. 773-774, Vol. 47, Issue 9, September 2015

Ng C S H, Lau K K W, Gonzalez-Rivas D, Rocco G. Evolution in Surgical Approach & Techniques for Lung Cancer. Thorax 2013; 68:681

Chiu P W Phee S J, Wang Z, Sun Z, Poon C C, Yamamoto T, Penny I, Wong J Y, Lau J Y, Ho K Y. Feasibility of full-thickness gastric resection using master and slave transluminal endoscopic robot and closure by overstitch: a preclinical study. Surgical Endoscopy 2014 January; 28(1):319-24.

Chiu P W, Wai Ng E K, Teoh A Y, Lam C C, Lau J Y, Sung J J. Transgastric endoluminal gastrojejunostomy: technical development from bench to animal study. Gastrointestinal Endoscopy 2010; 71(2):390-3.

Ng C S H, Wong R H L, Lau R W H, Yim A P C. Single Port Video-Assisted Thoracic Surgery: Advancing Scope Technology. Eur J Cardiothorac Surg 2015; 47(4):751

Ng C S H, Rocco G, Wong R H L, Lau R W H, Yu S C H, Yim A P C. Uniportal and Single Incision Video Assisted Thoracic Surgery—The State of the Art. Interact Cardiovasc Thorac Surg 2014; 19(4):661-6

Ren H L, Lim C M, Wang J, Liu W, Song S, Li Z, Herbert G, Tse Z T H, Tan Z. Computer Assisted Transoral Surgery with Flexible Robotics and Navigation Technologies: A Review of Recent Progress and Research Challenges. Critical Reviews in biomedical engineering 2013; 4:365-391

Valentina Vitiello, Lee S L, Cundy T P, Yang G Z. Emerging robotic platforms for minimally invasive surgery. IEEE Reviews in Biomedical Engineering 2013; 6:111-126

H. Keller et al., Method for navigation and control of a magnetically guided capsule endoscope in the human stomach. The fourth IEEE RAS/EMBS international conference on biomedical robotics and biomechatronics, Roma, Italy. June 24-27, 2012, p. 859 ff.

U.S. Pat. No. 6,902,528 B1. Method and apparatus for magnetically controlling endoscopes in body lumens and cavities, Jun. 7, 2005.

U.S. Pat. No. 8,084,898 B2. Magnetic actuator, magnetic actuator operating method, and capsule endoscope using the same, Dec. 27, 2011. (Olympus)

SUMMARY OF THE INVENTION

This disclosure provides a new endoscope for minimal invasive surgery. It is shaftless, wireless, and can be steered inside the body, operating in a remote manner. Compared with existing endoscopes, it neither requires additional incision nor does it occupy trocar or port space. Without the endoscope shaft, the surgical access trauma and incisions size can potentially be reduced, avoiding endoscope-instrument fencing. It can be placed remotely from the access incision, providing an improved and wider field of view. It is soft-bodied and compact in structure, therefore safety is high. More than one wireless endoscope can be placed into the operating cavity, providing simultaneous multiple video images of different viewing angles. These features allow safer, more efficient and less traumatic surgery by reducing trocar size or number.

The endoscopic system of this invention comprises multiple components which may be sold and used separately or together in any combination. Although initially inspired for use in laparo-endoscopic single-site surgery, the components of the system can be used for any type or surgery for which they are suitable.

One component is a wireless steerable endoscope configured to go inside the body of a human or non-human patient, receive optical images of a tissue or cavity of interest, and transmit the optical image wirelessly to a receiver outside the body. The endoscope can include a communications module configured to transmit and/or receive data. The image is typically transmitted in "real time", which means that the surgeon may collect the image by adjusting orientation of the imaging module, and see the results on a display within a matter of seconds. In addition or in the alternative, the image may be recorded for later review. The endoscope includes a base configured for securing to an inner surface of a body cavity, to which is mounted an optical imaging module. Typically, there is also a housing mounted on the base to contain and support the optical imaging module.

The wireless steerable endoscope is generally made of a soft or pliable material that is physiologically compatible with a human or animal body and is chosen to facilitate insertion and reduce damage to surrounding tissues. Optionally, the module is removable from the housing for purposes of cleaning or maintenance, or to exchange with a different module having different optics. In some embodiments, the housing has an opening through which to exchange optical modules (such as at the end facing outwards from the base), and the module is encased within a second housing or covering that fits securely in the outer housing mounted on the base. In some embodiments, the outer housing can be cylindrical in shape with the imaging module being cylindrical and sized to fit snugly inside the housing. Various other shapes may be used so that the shape of the housing matches the shape of the module so as to provide a snug fit and minimize empty space within the housing.

In some embodiments, another component is an external magnetic controller that contains a means for remotely adjusting the position and/or the orientation of the endoscope within the patient. Typically, the controller has a base or a structure configured for securing on or near an outer surface of the body cavity which contains the endoscope. Except for the controlling magnets contained within, the controller is made of a non-ferrous material. The controlling means in the controller can comprise one or more controlling magnets of sufficient strength such that when the external magnetic controller is secured on or near the outer surface or skin, the wireless steerable endoscope is magnetically secured to the inner surface of the body cavity by way of an anchoring feature, such as a magnet in the endoscope (typically in the base). It is appreciated that some embodiments may utilize various other anchoring features (e.g. barbs, geometric anchors), as would be known to one of skill in the art.

The steerable endoscope often also have an orientating mechanism for tilting the housing or the imaging module in relation to the base of the endoscope so as to change the orientation of the optical imaging module to get a different view of the internal cavity in which it is secured. Typically, the orientating mechanism is actuatable from outside the body by an external controller. Such orientating mechanism can including any of: one or more flexible members, cables, hypotubes, gears, sliding members, joints, other suitable means, or any combination thereof. In some embodiments, the orientating or tilting mechanism is one or more flexible members or joints situated between the base portion and the housing or the lens of the optical imaging module. A flexible member for adjustable tilting in two dimensions around the endoscope can be constructed as a column or connector made of a pliable material. Alternatively, suitable joints for adjustable tilting in two dimensions include a ball-and-socket joint, or a plurality of sliding connectors around the periphery or circumference of the housing or imaging module.

The external magnetic controller has a means for remotely and variably controlling the orientation of the optical imaging module by causing the housing or outer portion of the endoscope to tilt in one direction or another at the discretion of the operator. The external controller is adjustable to change magnetic force exerted on one or more steering magnets situated in the endoscope, thereby changing the tilt or the orientation of the endoscope. The steering magnets in the endoscope are typically situated in or around the periphery of the endoscope or in the housing. The external controller has a corresponding controlling magnet in the external controller that is adjustable in position within the external controller so as to change magnetic force exerted on the steering magnets in the endoscope.

In some embodiments of the invention, different external magnets are used to anchor the endoscope inside the patient and to tune orientation of the optical module. For simplicity in construction and operation, the same controlling magnet performs both a securing function by interacting with the anchoring magnet in the endoscope, and an orientation function by interacting with the steering magnets. Thus, the position of the endoscope on the inner surface of the cavity can be adjusted by sliding the controlling magnet over the skin. The orientation of the optical module can be controlled by a combination of lateral positioning and height of the controlling magnet.

To allow adjustments to be made, the controlling magnet can be mounted so as to be moveable in three dimensions in relation to the site of the endoscope. For example, it can be mounted in a cylindrical housing perpendicular to the base of the external controller, with a position that is adjustable both radially and circumferentially within the cylindrical housing. The external controller can be open such that the controlling magnet is circumferentially adjustable by way of a shaft that moves circumferentially about the cylinder's radial axis, and is radially adjustable by rotating the shaft through a screw or sliding joint. Typically, the position or height of the controlling magnet is also adjustable axially within the cylindrical housing by way of a second shaft positioned radially in the housing. In a second example, the external controller can have one, two, three, or four or more controlling magnets on a platform that is moveable so as to adjust the pitch, roll, and height of the platform in relation to the base or the subject, and/or is tiltable so as to adjust orientation of the field emanating from the magnets.

The magnets inside the endoscope are usually fixed or permanent magnets, such as may be manufactured from a ferrous material. The controlling magnet(s) may be fixed or permanent magnets, or they may be chargeable magnets (for example, electromagnetic coils or solenoids). This gives the user an additional mode of controlling the endoscope by adjusting power to the magnetic coils. In the endoscope, the base, the housing, and the covering on the optical module may be made of a pliable material (such as silicon rubber) having a low Young's modulus, having sufficient softness and pliability to avoid additional trauma to the subject while maintaining integrity of the endoscope and protecting inner components.

Internal features of the endoscope or the optical imaging unit may include a combination of any of the following: (1) a camera such as a CCD camera or other pixilated light receiver to obtain a two-dimensional optical image of the view from the imaging module, (2) a charging module configured to receive power wirelessly when the endoscope is in use, (3) a power storage unit (usually a battery), (4) a source of illumination to light the tissue or cavity being imaged, (5) a transmitter for wirelessly sending the image to a receiver outside the body, and (6) electronics such as a microprocessor electronically connected and programmed to control such matters as the degree or color of illumination, the focus of the imaging module, power management, and data collection and transmission. The optical imaging module typically has a transparent openings or surface such as a dome that has a hydrophobic coating, which provides a means by which light from the illuminator can be shone upon the tissue, and through which light can be collected and thereafter assembled into an optical image.

The system may have more than one wireless steerable endoscope. The multiple endoscopes can be independently controlled by one or more external controllers or can be configured to move in a coordinated manner by an external controller based on each other's movement. Typically, they are each controllable by a separate control magnet and provide separate views concurrently from inside the body cavity. The images may be displayed as multiple views, or assembled into a three-dimensional image.

The endoscopic system of this advice typically also has an external electronics module wirelessly and electronically connectable to the endoscope so as to receive a moving optical image from the optical imaging module and display it to a user. The electronics module may comprise any combination of the following: (1) a receiver to receive image data wirelessly from the endoscope and assemble it into a digital image, (2) a transmitter to transmit information to a receiver in the endoscope to control or adjust its components, such as the illumination system and the camera, (3) a display screen to show the optical image to the user, (4) a data recorder, and (5) a microprocessor configured and programmed to control and operate components of the endoscope.

The external magnetic controller may be motorized so that positioning of the endoscope may be machine controlled. The electronics for controlling the motors is contained in the external electronics module described in the preceding paragraph, or in a separate housing. Instructions may be transmitted from the electronics to the controller by interconnecting electronics or wirelessly. The electronics can include a microprocessor that is programmed to adjust the position of the control magnet, thereby adjusting the position and orientation of the imaging system in the endoscope. The control electronics may be instructed by the user, or may be programmed in advance to carry out a particular series of movements in accordance with a surgical protocol, optionally adjusting the series of movements in response to the images obtained.

This invention also provides a method of using an endoscopic system in a surgical procedure on a human or non-human subject. The method nominally comprises securing a wireless steerable endoscope inside a body cavity in the subject, obtaining an image therefrom, and conducting the surgery in accordance with what is shown in the optical image. This is exemplified by the following steps: (1) creating a surgical incision in the subject, and then in any order: (2) passing the wireless steerable endoscope through the incision into the body cavity, (3) placing or securing the external magnetic controller on the outside surface of the body cavity or on or near the patient's skin, and (4) adjusting the external magnetic controller so as to position and/or secure the endoscope to the inner surface of the body cavity.

Before or after installation of the endoscope, surgical instruments can be introduced through the same or a different surgical incision. An optical image is wirelessly obtained from the endoscope and shown on the display. Optionally, the procedure includes adjusting the positioning or field of the external magnetic controller so as to change orientation of the endoscope during the surgery, thereby adjusting the viewpoint of the image Surgical methods of this invention include laparo-endoscopic single-site (LESS) surgery, single port access (SPA) surgery, video-assisted thoracoscopic surgery (VATS) surgery and natural orifice transluminal endoscopic surgery (NOTES). Exemplary but non-limiting body cavities in which the products and methods of the invention may be used include the thoracic cavity and the abdomen. The surgery may be conducted for diagnostic observation, ablation, tissue repair, tissue removal, application of pharmaceutical agents, or any suitable purpose.

Other embodiments and aspects of the invention will be apparent to the reader from the description that follows, the drawings, the examples, and the appended claims.

DETAILED DESCRIPTION

In minimally invasive surgery, one incision port is required for the endoscope or the endoscope enters the surgical site via the same port as the instruments. The field of view of existing endoscopes is often restricted by the limited steerability of the distal camera. Furthermore, the endoscope often causes fencing with other instruments either within the operating space or at the incision site if the endoscope is sharing the port with another instrument.

To reduce the surgical access trauma and save space for the operation of other surgical instruments, an improvement is to have a shaftless endoscope, which can be steered inside the body cavity of the surgical site and most importantly is safe.

This disclosure provides a wireless steerable endoscope system. It is composed of an internal steerable endoscope, an external controller and the image/video display. The steerable endoscope contains one or more of the following components in any combination: a wireless transmit module, a power module, a magnetic module and a soft body. Typically, all the modules are encased in the soft body. The steerable endoscope is magnetically anchored inside the body cavity (for example, the thoracic cavity or the abdominal cavity) and can be steered and controlled by using magnetic force. The steering motion include sliding, rolling, or bending. Main advantages of this endoscope include: (1) it is shaftless and can be steered wirelessly using magnetic force, therefore reducing trauma and saving space for the surgical instruments; (2) it is soft bodied, therefore intrinsically safe.

Figure 1:
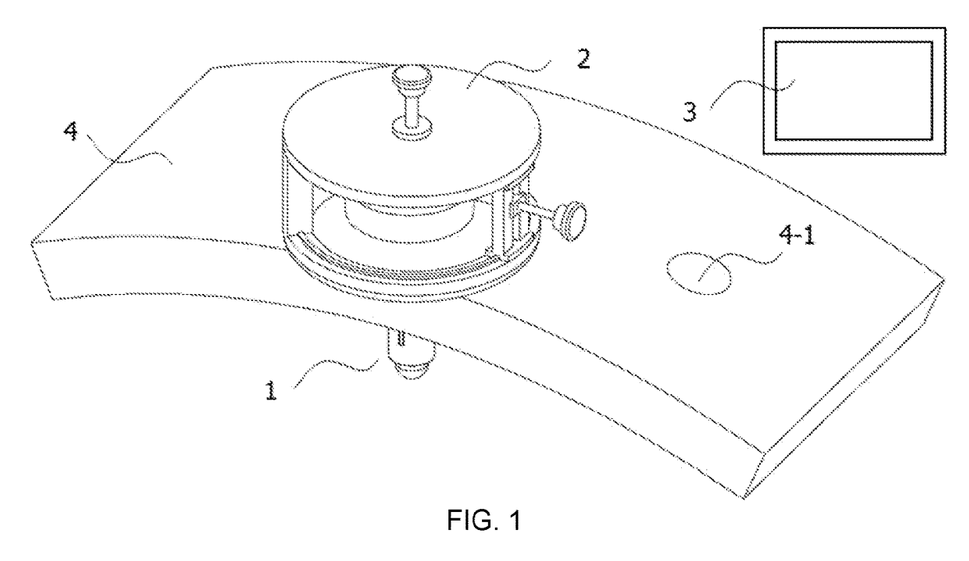
FIG. 1 is an orthogonal view of components of an exemplary wireless magnetically steerable endoscope system. These include the body of a wireless steerable endoscope 1 which has been inserted underneath the skin 4 into a body cavity by way of an incision/trocar/port 4-1. Also shown are the external magnetic controller 2 positioned on the surface of the skin 4, and the image/video display 3.

FIG. 1 is an illustration of a steerable endoscope according to the invention. The composition of the system is shown, i.e. the wireless steerable endoscope 1, the external magnetic controller 2 and the image/video display 3. The wireless steerable endoscope 1 could be inserted through the incision 4-1 on the body skin 4 and be anchored/steered inside the body cavity by the external magnetic controller 2. The images/video taken by the wireless steerable endoscope 1 is transmitted to the image/video display 3, which could be a normal LCD or flat-screen display with electronics configured to convert data received from the imaging system of the endoscope to an image. This endoscope system could be used in minimally invasive surgery (MIS), single port access (SPA) surgery and natural orifice transluminal endoscopic surgery (NOTES).

Figure 2:
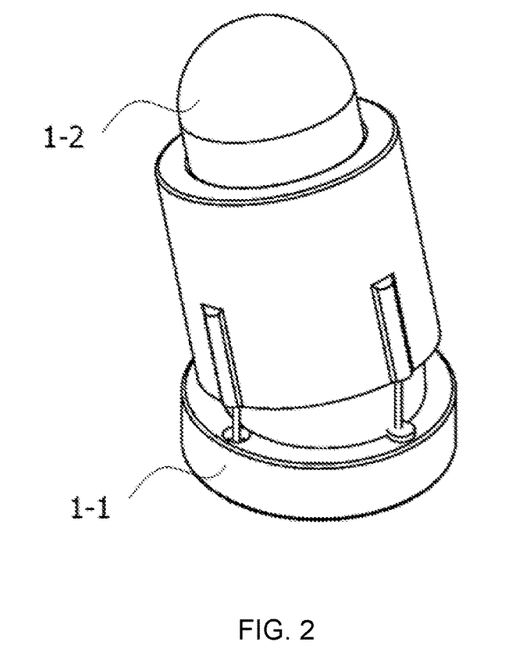
FIG. 2 is an orthogonal view of the wireless steerable endoscope, in which the soft steerable module 1-1 contains and supports the image module 1-2.
Figure 3A:
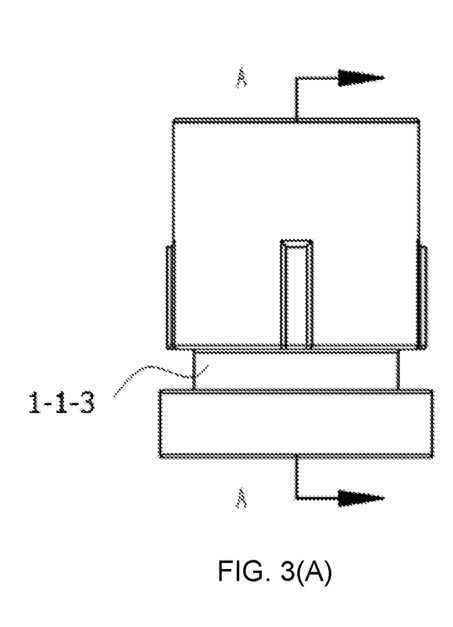
FIGS. 3(A) to 3(D) are respectively a side view, a cross-sectional view, a top-down view, and a perspective view of a soft steerable module 1-1 in the first configuration.
Figure 3B:
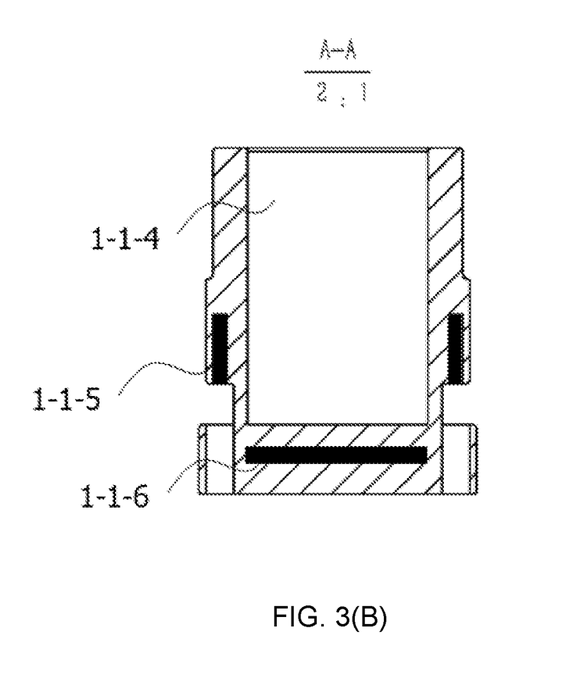
Figure 3C:
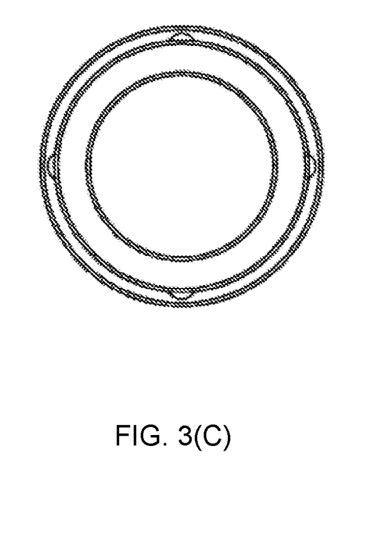
Figure 3D:
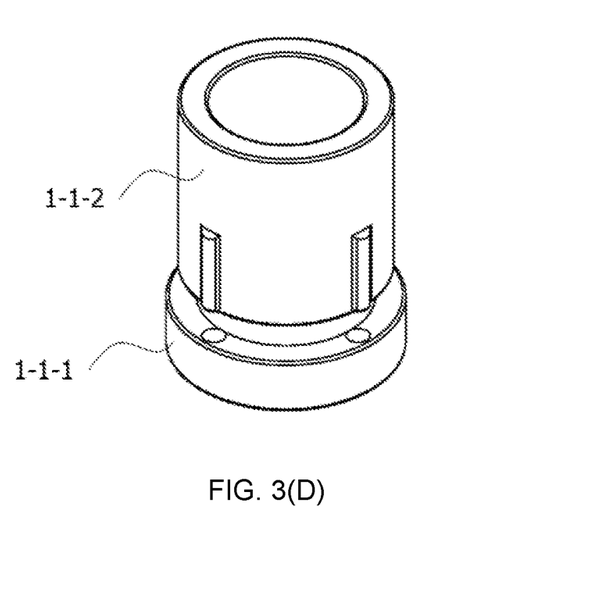
Figure 11A:
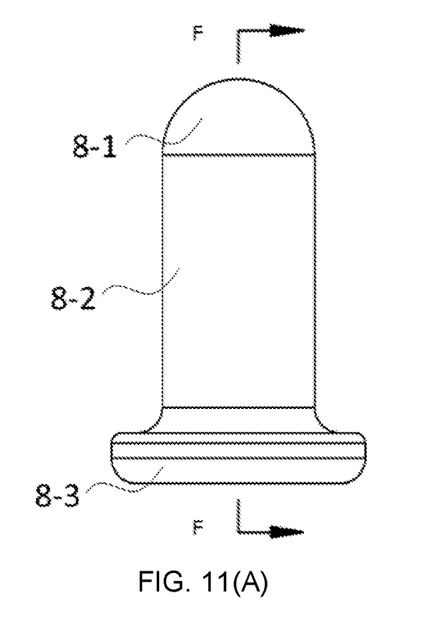
FIGS. 11(A), 11(B), and 11(C) are respectively a side view, a cross sectional view, and a top view of a one-piece embodiment of the wireless steerable endoscope, comprising the optical dome 8-1, the endoscope body 8-2, the base 8-3, the imaging and lighting module 8-4, the power module 8-5, the wireless transmission module 8-6, the wireless charging module 8-7 and the magnets 8-8.
Figure 11B:
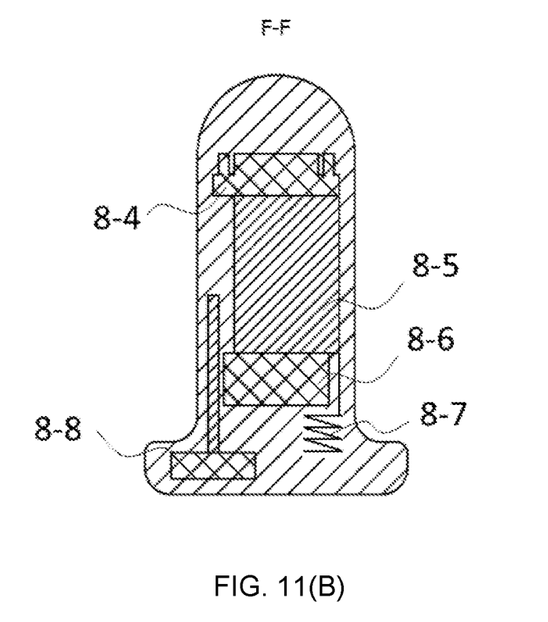
Figure 11C:
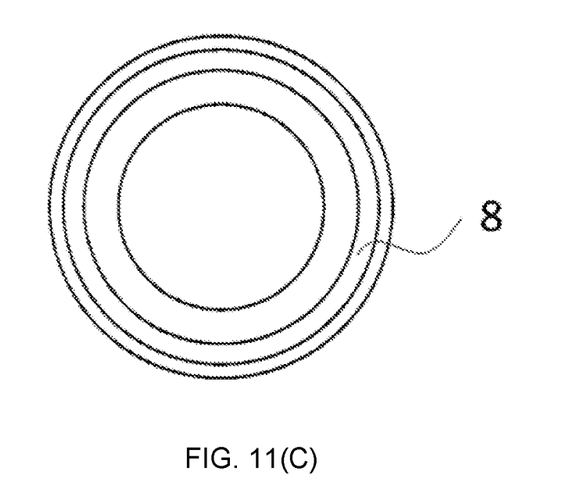

The wireless steerable endoscope 1 is composed of the soft steerable module 1-1 and the imaging module 1-2, as shown in FIG. 2. The soft steerable module 1-1 contains and supports the image module 1-2. There could be two types of configurations. The first configuration is the soft steerable module 1-1 and the image module 1-2 are separated. The image module 1-2 could be inserted into the soft steerable module 1-1. One example is using a capsule endoscope as the image module 1-2. The second configuration is the image module 1-2 is built inside the soft steerable module 1-1, or they be a one-piece component. One example is shown in FIG. 11, discussed below The advantage of the configuration shown in FIG. 2 is that image modules 1-2 with different performance, for example, focal length, field of view, or resolution could be replaced according to the task requirement. For the configuration shown in FIG. 11, sterilization is simpler.

FIGS. 3(A) to 3(D) give one example of the soft steerable module 1-1 in the first configuration. Main feature include the base 1-1-1, the socket 1-1-2, the bending section 1-1-3, the chamber 1-1-4, the steering magnets 1-1-5 and the anchoring magnet 1-1-6. The material used for the soft steerable module 1-1 have low Young's modulus and is bio-compatible, examples include silicon rubber or Ecoflex™. Typically, the Young's modulus is below 1, 0.5, or 0.1 GPa, typically 0.001 to 0.01, 0.01 to 0.1, or 0.1 to 1 GPa. The anchoring magnet 1-1-6 is embedded inside the base 1-1-1. The force between the anchoring magnet 1-1-6 and the external magnetic controller 2 presses against the base 1-1-1 to the wall of the body cavity. By moving the external magnetic controller 2, the base 1-1-1 could glide along the wall of the body cavity. The steering magnets 1-1-5 are embedded inside the socket 1-1-2. The bending section 1-1-3 connects the base 1-1-1 and the socket 1-1-2. It has a small bending stiffness and could be bent easily.

Figure 4A:
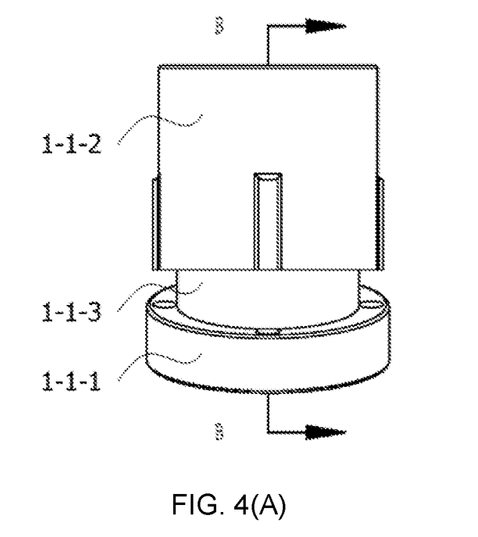
FIGS. 4(A) and 4(B) are respectively a perspective view and a cross-sectional view of the soft steerable module 1-1 in a bent configuration without the image module.
Figure 4B:
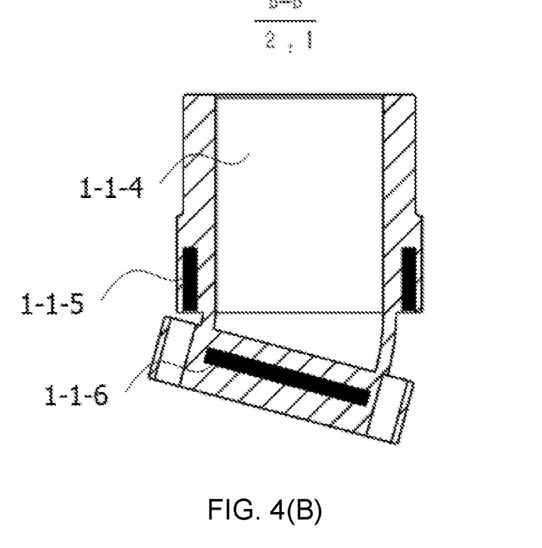

At a resting position, the magnetic force between the steering magnets and the external magnetic controller 2 is co-axial with the bending section. As a result, the bending section 1-1-3 is straight. By controlling the magnetic field using the external magnetic controller 2, the force exerted to the steering magnets 1-1-5 is biased, which generates a bending moment to the bending section 1-1-3. This bending moment causes the bending section 1-1-3 to bend or tilt and changes the orientation of the socket 1-2. The bending angle depends on the amplitude of the bending moment and the bending direction depends on the direction of the bending moment. FIGS. 4(A) and 4(B) show the soft steerable module 1-1 in a bent configuration.

Figure 5A:
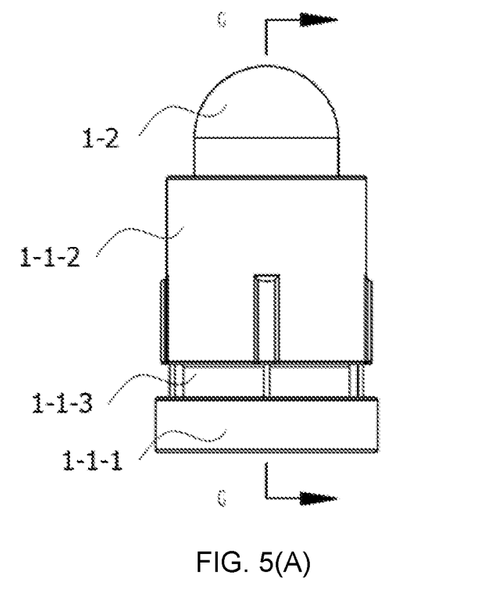
FIGS. 5(A) and 5(B) are respectively a side view and a cross-sectional view of the soft steerable module 1-1 with the image module 1-2 fitted into the central chamber.
Figure 5B:
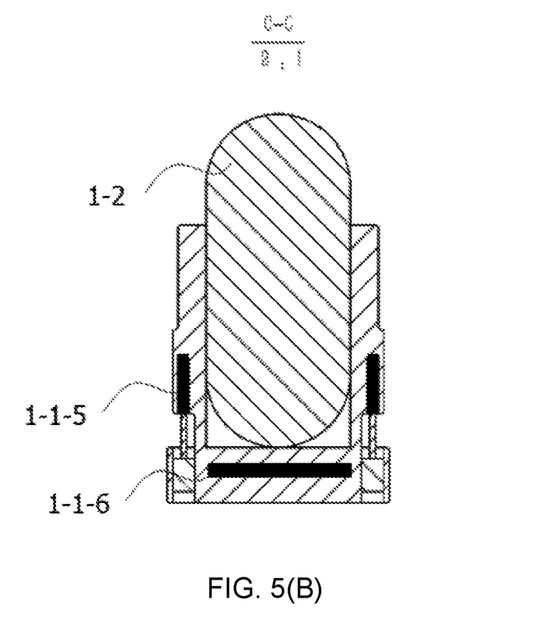
Figure 6A:
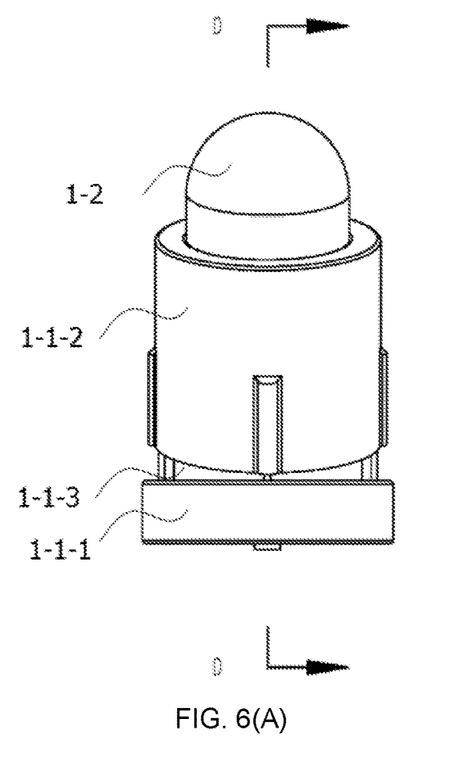
FIGS. 6(A) and 6(B) are respectively a perspective view and a cross-sectional view of the soft steerable module containing the image module as it changes orientation.
Figure 6B:
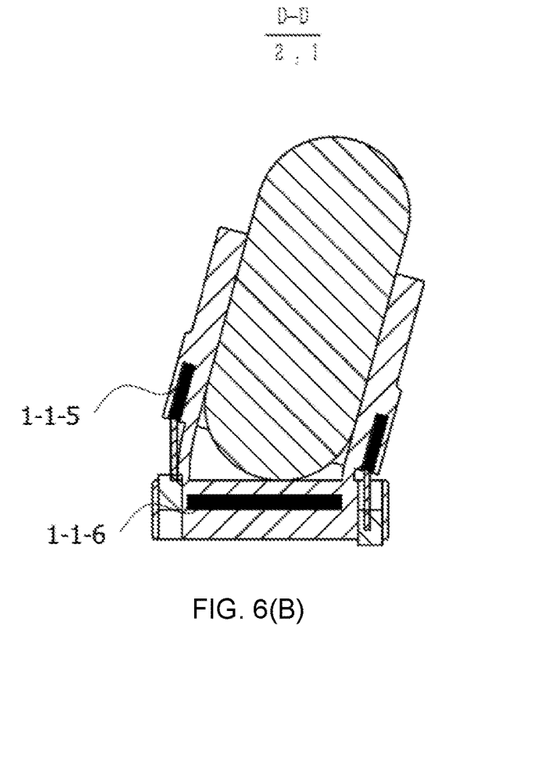
Figure 7A:
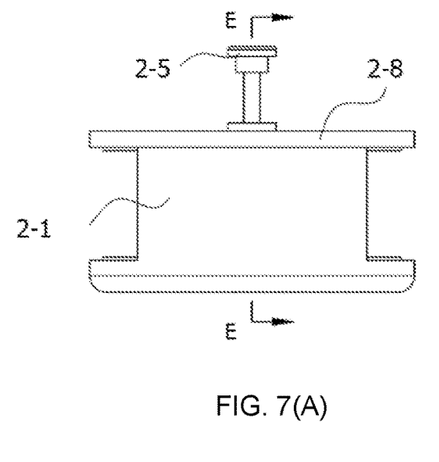
FIGS. 7(A) and 7(B) are respectively a side view and a cross-sectional view of the external magnetic controller 2-1.
Figure 7B:
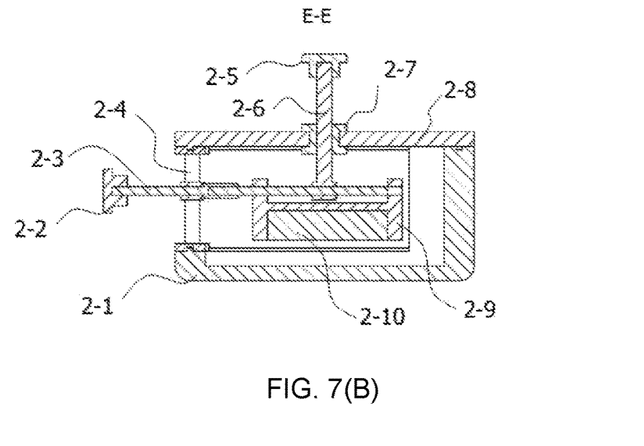
Figure 8A:
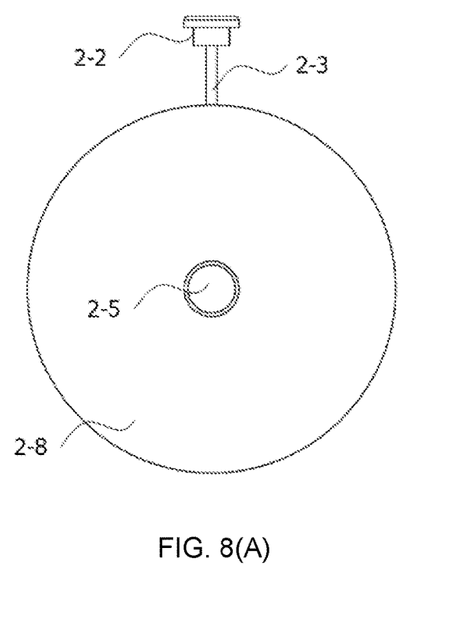
FIGS. 8(A) and 8(B) are respectively a top-down view and a cross-sectional view of the external magnetic controller 2-1.
Figure 8B:
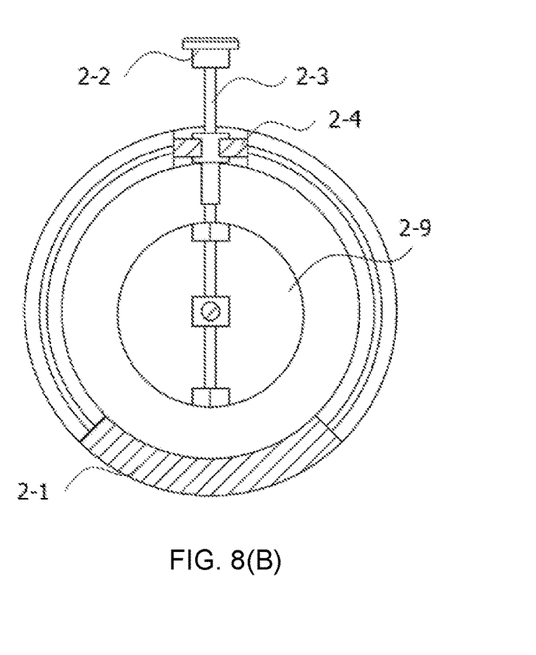
Figures 9A, 9C:
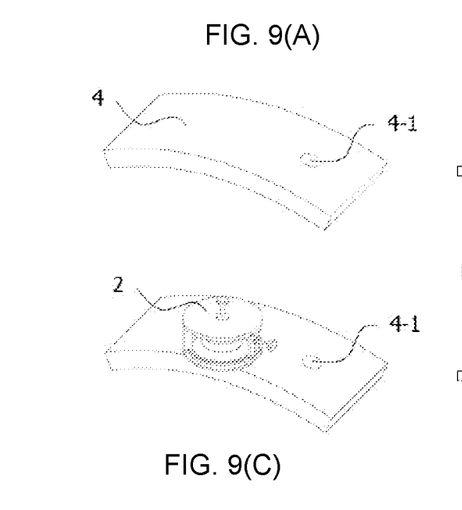
FIGS. 9(A) to 9(E) constitute a flow chart showing perspective views that illustrate a surgical procedure to implant a wireless endoscope system. In step I, the wireless steerable endoscope 1 is inserted through the skin 4 into a body cavity. In step II, the external magnetic controller 2 is placed on top of the skin 4 and close to the surgical site 7. In step III, the wireless steerable endoscope 1 is secured to the wall of the body cavity from the inside by the external magnetic controller 2. In step IV, surgical instruments 5 and 6 are introduced to the surgical site 7 via the same incision/trocar/port 4-1.
Figures 9B, 9D:
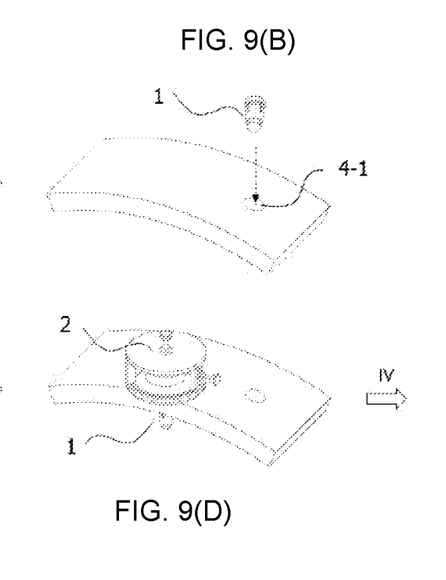
Figure 9E:
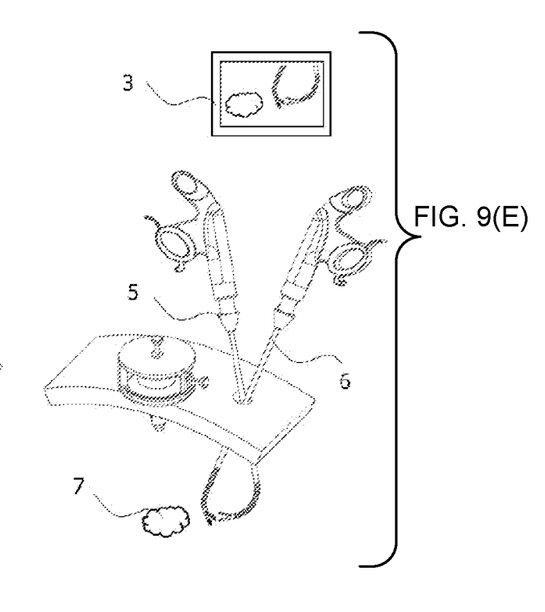

The image module 1-2 is plugged into the chamber 1-1-4 of the soft steerable module 1-1, as shown in FIGS. 5(A) and 5(B). Its moves along with the socket 1-1-2. The viewing direction of the image module 1-2 is coaxial with the socket 1-1-2. The image module 1-2 fits tightly into the chamber 1-1-4. When the soft steerable module 1-1 glides along the wall of body cavity and bends to all directions, the image module 1-2 is held tightly by the socket 1-1-2 and won't fall off during the manipulation. FIGS. 6(A) and 6(B) show the image module 1-2 as it changes orientation.

FIGS. 7(A), 7(B), 8(A) and 8(B) show the external magnetic controller 2. It is composed of the main frame 2-1, the radial adjusting knob 2-2, the radial shaft 2-3, the circumferential slider 2-4, the axial adjusting knob 2-5, the axial shaft 2-6, the axial screw 2-7, the cover 2-8, the magnet holder 2-9 and the magnet 2-10. The magnet 2-10 is held by the magnet holder 2-9, which is connected to the axial shaft 2-6 and the radial shaft 2-3. The axial position of the magnet holder 2-9 is controlled by the axial adjusting knob 2-5. Therefore, by placing the magnetic controller 2 to the top of the skin 4, the distance between the magnet 2-10 and the wireless steerable endoscope 1 can be controlled. The radial distance of the magnet holder 2-9 is controlled by the radial adjusting knob 2-2. The rolling of the magnet 2-10 is controlled by the circumferential slider 2-4. Pitch and yaw of the magnet 2-10 is controlled by the radial shaft 2-3 and the circumferential slider 2-4 together. This enables the adjustment of the relative position and orientation of the magnet 2-10 to the wireless steerable endoscope 1. Therefore, the amplitude and direction of the magnetic forces between the magnet 2-10 and the anchoring magnet 1-1-6 and the steering magnets 1-1-5 are controlled. The magnetic forces anchors the wireless steerable endoscope 1 to the wall of the body cavity, steers the wireless steerable endoscope 1 to glide along the wall of the body cavity and viewing different directions.

Once the external magnetic controller 2 has been secured on or near the skin with the endoscope underneath (not shown), the surgeon can then position the endoscope at a desired location and at a desired angle using the controller. The sliding of the endoscope beneath the skin can be achieved by moving the entire external controller 2 in a horizontal direction over the surface of the skin. By adjusting the radial adjusting knob 2-2, the radial shaft 2-3, and the circumferential slider 2-4, the endoscope and the magnet 2-10 can be purposely misaligned with the endoscope, whereby the tilting angle of the endoscope underneath the skin is controlled by the amount of misalignment. The distance between the endoscope and the magnet inside the controller can be adjusted to control the anchoring force. Thus, once the endoscope has been positioned appropriately, it can be secured in place by adjusting the axial adjusting knob 2-5. The position of the endoscope can be further adjusted during the surgery that follows so as to optimize the view captured by the endoscope during each step of the procedure.

FIGS. 9(A) to 9(E) constitute a flow chart showing perspective views that illustrate a surgical procedure to implant a wireless endoscope system. Typically, the endoscope 1 is put inside the body cavity first, and then positionally adjusted and anchored using the external controller 2. In step I, the wireless steerable endoscope 1 is inserted through the body cavity via the incision/trocar/port 4-1. In step II, the external magnetic controller 2 is secured on or near the skin 4 and close to the surgical site 7. For example, the external magnetic controller 2 can be secured above but close to the skin using an assistive device such as a passive/ active holder (not shown). In step III, the wireless steerable endoscope 1 is anchored to the wall of the body cavity by way of the external magnetic controller 2. The surgeon can use surgical graspers or similar implements to assist the anchoring: for example, placing the endoscope to the target position and then securing the external controller above the skin on or near the location of the endoscope beneath the skin, and then adjusting the magnets in the controller to achieve anchoring and steering into the desired location. In step IV, other surgical instruments 5 and 6 are introduced to the surgical site 7 via the same incision/trocar/port 4-1 to carry out the desired procedure. The wireless steerable endoscope 1 is steered to view the surgical site 7 and the image/video is transmitted to the image/video display 3 wirelessly.

Figure 10:
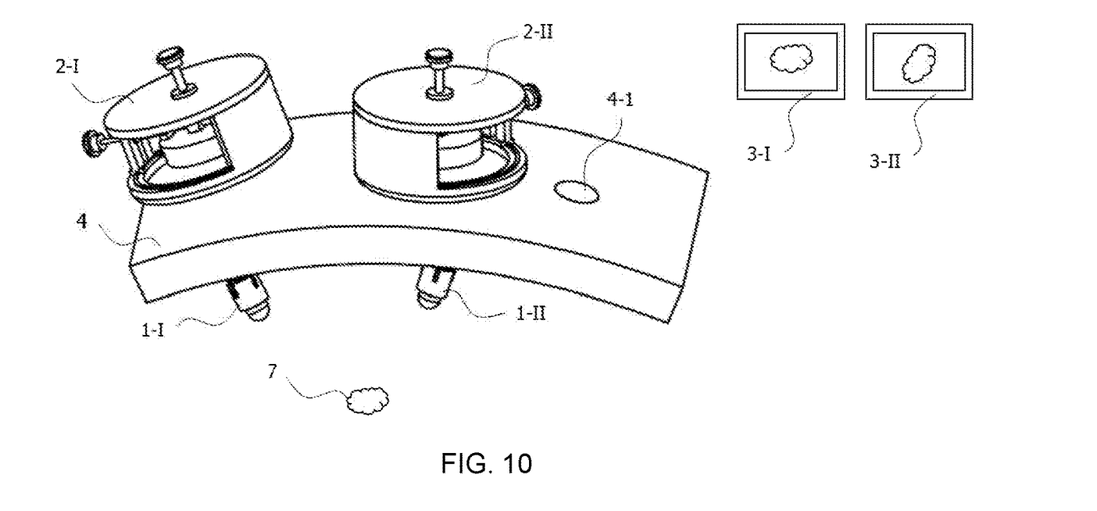
FIG. 10 is a perspective view showing to different wireless steerable endoscopes 1-I and 1-II inside a body cavity underneath the skin 4, each with its own external magnetic controller 2-I and 2-II respectively on the surface of the skin 4, and its own monitor 3-I and 3-II.

Multiple wireless steerable endoscopes 1 could be inserted through the body cavity via the incision/trocar/port 4-1, as shown in FIG. 10. Each wireless steerable endoscope 1 provides a view of the surgical site 7 from a different direction. All the images could be transmitted to the image/video display 3 simultaneously. These images could be displayed separately or they could form a stereo image or holographic view.

FIGS. 11(A), 11(B), and 11(C) show another example of the wireless steerable endoscope according to this invention. It is composed of the optical dome 8-1, the endoscope body 8-2, the base 8-3, the imaging and lighting module 8-4, the power module 8-5, the wireless transmission module 8-6, the wireless charging module 8-7 and the magnets 8-8. The optical dome 8-1 is hemi-spherical, transparent and coated with hydrophobic coating. The hydrophobic coating reduce the fogging and blood contamination during the operation. The imaging and lighting module 8-4 is similar to that of the conventional endoscopes. The wireless transmission module 8-6 is similar to that in the conventional capsule endoscopes. The power module 8-5 can be a rechargeable battery, although it is appreciated that the power module can be a capacitor or any suitable power storage component. It is connected to the wireless charging module 8-7, which is based on the electromagnetic induction principle. The power module 8-5 is typically charged before the operation and could also be charged during the surgical operation as required. The magnets 8-8 is used to anchor and steer the endoscope body 8-2. Their configuration is similar as in the previous embodiment. These components are encased in the endoscope body. The wireless steerable endoscope is therefore a single piece. The endoscope body 8-2 and the base 8-3 are both made of soft, bio-compatible material, for example, silicon rubber. Therefore, during the surgical operation the injury from the wireless steerable endoscope is eliminated.

Figure 12:
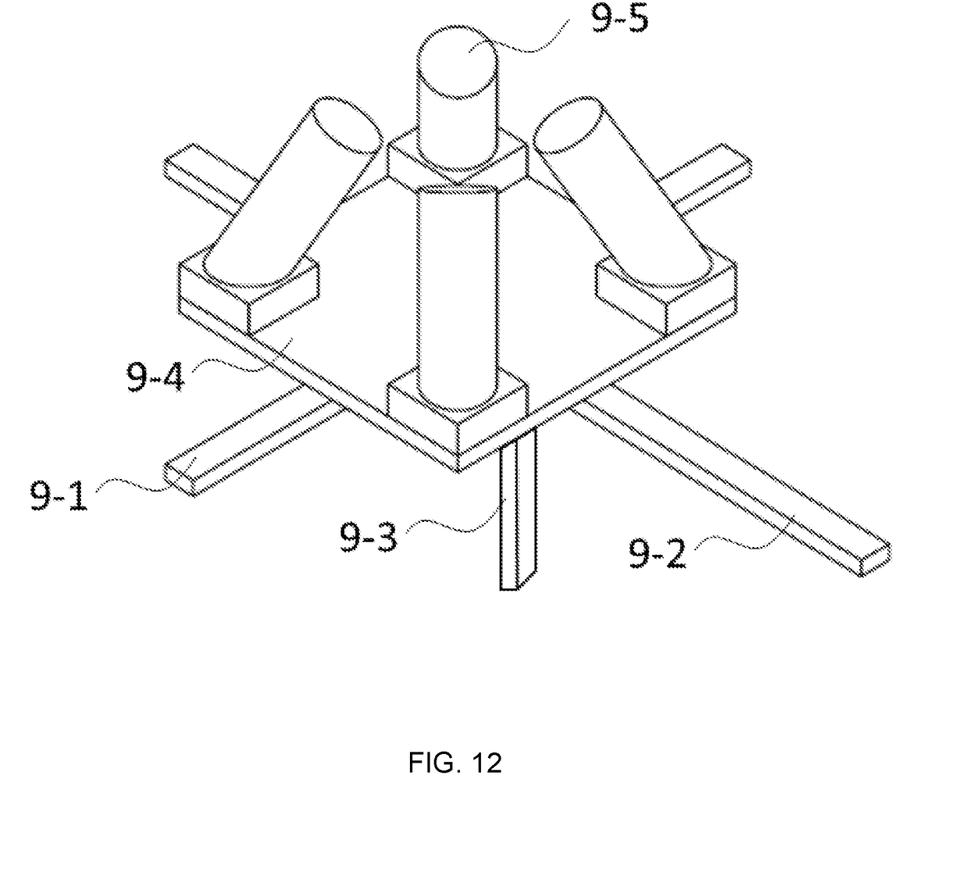
FIG. 12 is an orthogonal view showing another embodiment of the external magnetic controller, comprising a movable stage 9-4 and four electromagnetic coils 9-5.

FIG. 12 shows another embodiment of the external magnetic controller. It is composed of the transversal rail 9-1, the longitudinal rail 9-2, the vertical rail 9-3, the moving stage 9-4 and the electromagnetic coils 9-5. The electromagnetic coils 9-5 are placed onto the moving stage 9-4, which could move in three independent directions along the rails. A number of electromagnetic coils 9-5 (four are shown in the figure) are used to generate a magnetic field. The amplitude and direction of the magnetic field could be controlled by the current in the electromagnetic coils 9-5. As the magnetic strength is highly dependent on the distance to the magnetic source, therefore the range of magnetic steering is limited. In this embodiment, the electromagnetic coils 9-5 are placed onto the moving state 9-4 to increase the steering range. The movement of the moving stage 9-4 could be controlled by common techniques, for example, a DC motor with screw or linear motor.

In summary, the invention can include any of the following features in any combination: One or multiple internal steerable endoscopes, an external controller and an image/video display. It is magnetically anchored inside the body cavity (e.g. thoracic cavity or abdominal cavity) and can be steered using magnetic force. The steering motion can include sliding, rolling, or bending in any combination. The image module typically contains the image sensor, illumination unit and a transparent dome with hydrophobic coating. The coating prevents fogging and blood contamination. Image/video is transmitted wirelessly to the display through the wireless transmit module. The power module provides power supply to the image module and wireless transmit module. It can be in the form of battery or with a wireless charging system.

The magnetic module contains one or multiple magnetic material: typically a permanent magnet made of ferrous or some other magnetic material. The external controller provides a controllable magnetic field. This magnetic field could be generated by a permanent magnet with adjustable position or by mobile and intensity-adjustable electromagnetic coils. The movement of the magnet can be controlled manually or using motors with proper interface (such as a joystick). The current supply and movement of the electromagnetic coils are calculated according to the required magnetic field. The image/video display can be in the form of LCD screen or projector or by holography. Multiple steerable endoscopes could be inserted and be present within the operating cavity to provide simultaneous multi-direction views.

Figure 13A:
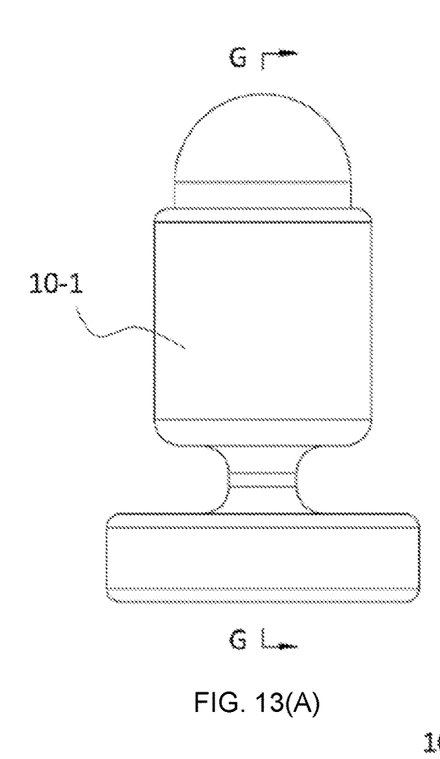
FIG. 13(A) and FIG. 13(B) show a side and cross sectional view, respectively, of another embodiment of the wireless steerable endoscope in a rest configuration, the endoscope having a soft steerable module 10-1, an image module 10-2, a fixed magnet 10-3, and an anchoring magnet 10-4.
Figure 13B:
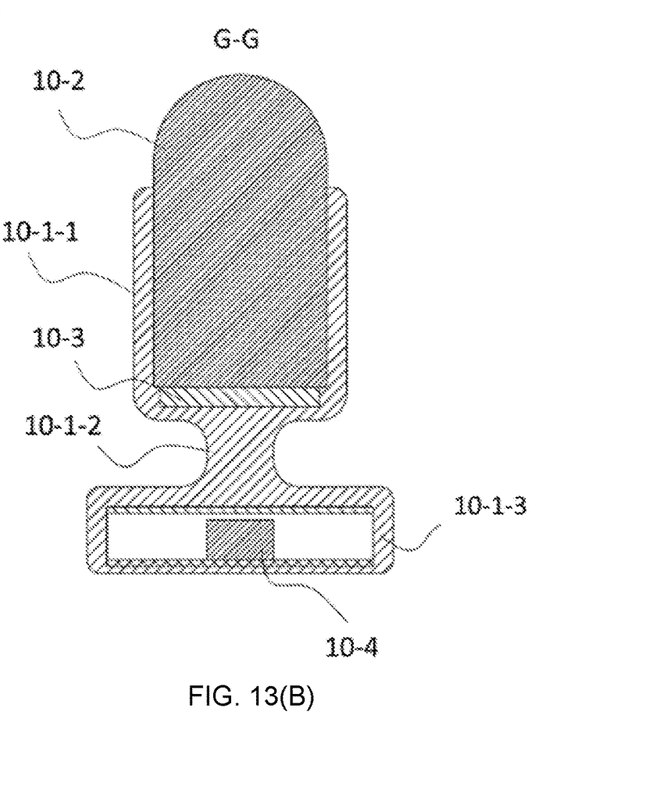

FIG. 13(A) and FIG. 13(B) show another embodiment of a wireless magnetically steerable endoscope. FIG. 13(A) shows a side view of the endoscope in a rest or non-bent configuration and FIG. 13(B) shows a cross sectional view along axis G-G. The wireless steerable endoscope has a soft steerable module 10-1, a image module 10-2, a fixed magnet 10-3, and an anchoring magnet 10-4. In this embodiment, the soft steerable module 10-1 includes three parts: the image module housing 10-1-1, the bending section 10-1-2 and the base 10-1-3. The fixed magnet 10-3 is embedded inside the image module housing 10-1-1 and the anchoring magnet 10-4 is contained inside a cavity of the base 10-1-3. The anchoring magnet 10-4 positioned inside the cavity of the base 10-1-3 is controlled by an external controller. In the rest position, the anchoring magnet 10-4 is configured to stay in the center of the base 10-1-3.

Figure 14A:
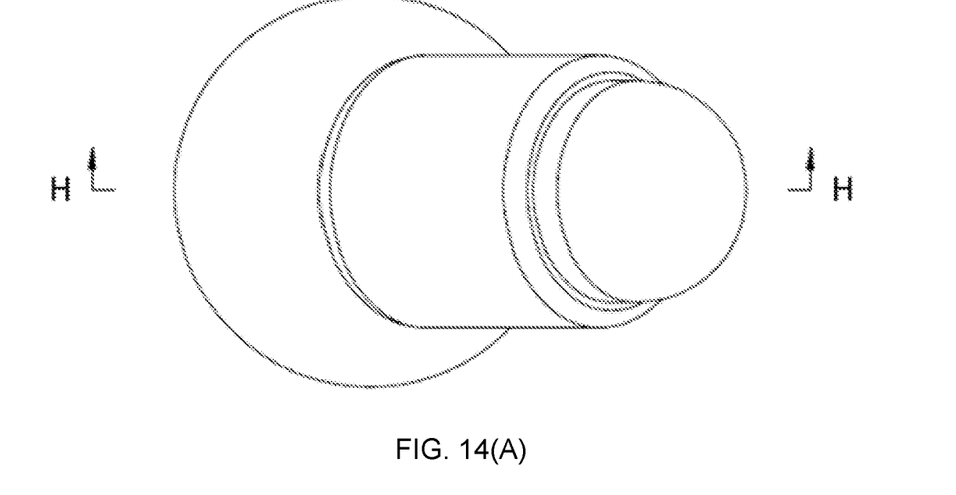
FIG. 14(A) and FIG. 14(B) show a perspective and a side cross sectional view, respectively, of the embodiment of the wireless steerable endoscope of FIG. 13(A) in a bent configuration.
Figure 14B:
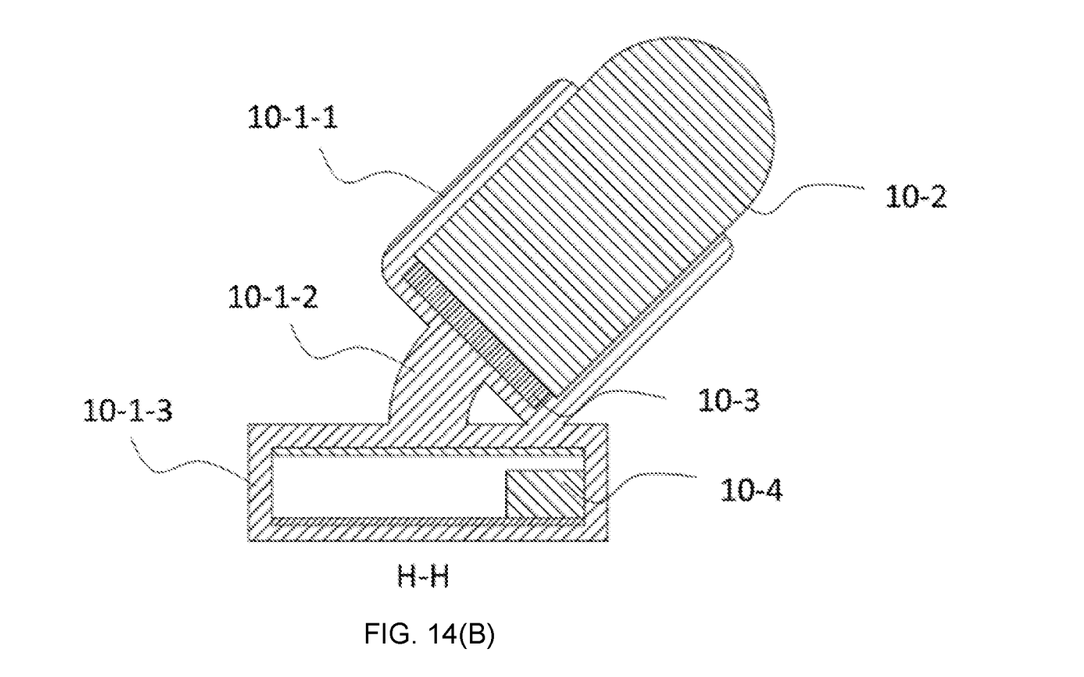

FIG. 14(A) shows the endoscope in a bent configuration and FIG. 14(B) shows a cross sectional view along axis H-H. By repositioning the anchoring magnet 10-4 within the base to an off-center position, the magnetic force between the anchoring magnet 10-4 and the fixed magnet 10-3 bends the bending section 10-1-2 to a desired orientation. This changes the orientation of the image module housing 10-1-1 and the image module 10-2. The viewing angle of the endoscope is therefore adjusted by use of the external controller.

The invention has been described and illustrated in this disclosure with reference to particular embodiments for the benefit and convenience of the reader. Discussion of various aspects of the device in the context of image guided radiation therapy does not limit its use to that context except where expressly indicated.

The devices and methods of the invention may be substituted and adapted for use in different contexts for different objectives using different materials, elements, and steps without undue experimentation, thus achieving any or all of the benefits of the invention without departing from the scope of what is claimed.

In the United States of America and elsewhere as permitted by law, each publication and patent document cited in this disclosure is incorporated into the disclosure by reference in its entirety for all purposes, to the same extent and effect as if each such publication or document was explicitly and individually indicated to be incorporated by reference.

What is claimed is:

1. An endoscopic system suitable for laparo-endoscopic single-site surgery of a subject in need thereof, wherein the system comprises:
    a wireless steerable endoscope that includes:
        an endoscope base configured for securing to an inner surface of a body cavity and configured for gliding across the inner surface of the body cavity;
        a housing having one end connected to the endoscope base via a flexible member and second end projecting outwards, wherein the flexible member is configured for reorienting the housing;
        an optical imaging module with communication functions that is configured to capture an optical image of the body cavity from the second end of the housing and to transmit the image wirelessly to a receiver outside the body cavity in real time;
        an anchoring magnet in the endoscope base configured for both anchoring and gliding the endoscope base and a set of magnets in the housing configured for reorienting the housing; and
    an external magnetic controller that includes:
        an external controller base configured for securing on or near an outer surface of the body cavity or to the skin of the subject; and
        one or more controlling magnets of sufficient strength such that when the external magnetic controller is on or near the outer surface or skin, the wireless steerable endoscope is magnetically anchored in a desired location against the inner surface of the body cavity by way of the anchoring magnet and is positionable to the desired location by moving the external controller base along the outer surface of the body cavity or the skin of the subject.

2. The system of claim 1, wherein the steerable endoscope further includes a means for tilting the housing in relation to the endoscope base so as to change the orientation of the optical imaging module; and wherein the external controller further includes a means for variably controlling the orientation of the optical imaging module by tilting the housing.

3. The system of claim 1, wherein the steerable endoscope is tiltable by way of the flexible member or joint between the endoscope base and the housing, thereby allowing orientation of the optical imaging module to be changed in relation to the endoscope base.

4. The system of claim 1, wherein the housing of the steerable endoscope further comprises one or more steering magnets, and the external controller has a controlling magnet that is adjustable within the controller so as to change magnetic force exerted on the steering magnets of the endoscope, thereby changing orientation of the optical imaging module.

5. The system of claim 4, wherein the controlling magnet is mounted in a cylindrical housing perpendicular to the external controller base, and the position of the controlling magnet is adjustable axially, radially and circumferentially within the cylindrical housing.

6. The system of claim 5, wherein the controlling magnet is circumferentially adjustable by way of a shaft that moves circumferentially about the cylinder's radial axis, and is radially adjustable by rotating the shaft through a screw joint.

7. The system of claim 5, wherein the position of the controlling magnet is adjustable axially within the cylindrical housing of the external controller by way of a second shaft positioned radially in the housing.

8. The system of claim 1, wherein the housing of the steerable endoscope further comprises one or more steering magnets, and the external controller comprises one or more controlling magnets on a platform that is moveable so as to adjust the pitch, roll, and height of the platform in relation to the external controller base.

9. The system of claim 1, wherein the external controller contains permanent magnets or electromagnetic coils or solenoids for controlling the magnetic field.

10. The system of claim 4, wherein the anchoring magnet, the steering magnet(s), and the controlling magnets are permanent magnets.

11. The system of claim 1, wherein the optical imaging module of the endoscope is encased in a covering so that the module is removable from the housing.

12. The system of claim 11, wherein the covering and the housing is made of a pliable material having a Young's modulus less than 0.1 GPa.

13. The system of claim 1, wherein the optical imaging module further comprises a charging module configured to receive and store power wirelessly when the endoscope is in use.

14. The system of claim 1, wherein the optical imaging module further comprises a source of illumination.

15. The system of claim 1, wherein the optical imaging module further comprises a transparent dome with a hydrophobic coating.

16. The system of claim 1, further comprising a display module electronically connectable to the endoscope so as to receive optical images from the optical imaging module and display them to a user.

17. The system of claim 1, comprising a plurality of wireless steerable endoscopes each controllable by a separate external magnetic controller, which when in use provide separate views concurrently from inside the body cavity.

18. The system of claim 1, wherein the external magnetic controller is motorized, and the system is computer controlled.

19. A wireless steerable endoscope as described in claim 1 for use in obtaining images from within a body cavity of a subject.

20. An external magnetic controller as described in claim 1 for use in securing and controlling a wireless steerable endoscope inside a body cavity of a subject.

21. A method of using an endoscopic system in surgery conducted on a human or non-human subject for laparo-endoscopic single-site surgery, the method comprising:

inserting the wireless steerable endoscope inside a body cavity, wherein the wireless steerable endoscope comprises a base having an anchoring magnetic;

gliding the base across the surface of the body cavity to a desired location in the body cavity with magnetic force by moving an external magnetic controller having one or more controlling magnets;

securing the wireless steerable endoscope inside a body cavity in the subject by magnetic force with the external magnetic controller; and conducting the surgery in accordance with an optical image obtained from the wireless steerable endoscope.

22. The surgical method of claim 21, comprising:

creating a surgical incision in the subject;

passing the wireless steerable endoscope through the incision into the body cavity;

placing the external magnetic controller on the outside of the body cavity or on or near the patient's skin;

adjusting the external magnetic controller so as to magnetically anchor the endoscope in the desired location against to the inner surface of the body cavity;

introducing surgical instruments through the same surgical incision;

obtaining an optical image from the endoscope wirelessly;

adjusting the external magnetic controller so as to adjust orientation of the endoscope, thereby adjusting the viewpoint of the image; and conducting the surgery in accordance with what is shown in the optical image.

23. The surgical method of claim 21, wherein the body cavity is the thoracic cavity or the abdomen.

24. A wireless steerable endoscope comprising: a base having an anchoring magnet for securing to an inner surface of a body cavity, wherein the base is configured for gliding across the inner surface of the body cavity and the anchoring magnet being of sufficient strength to anchor the wirelessly steerable endoscope in a desired location when magnetically coupled with one or more controlling magnetics in an external controller such that moving the external controller along the surface of the patient while magneticallu coupled with the endoscope within the body cavity moves the base to the desired location within the body cavity; an optical imaging module coupled with the base and configured to capture an optical image from within the body cavity in real time; a communication module configured for wirelessly transmitting the optical image; and an orientating mechanism configured to orient the optical imaging module relative the base so as to adjust a viewpoint of the optical image, the orienting mechanism being wirelessly actuatable from outside the body cavity.

* * * * *